United States Patent
Liang et al.

(10) Patent No.: US 6,942,617 B2
(45) Date of Patent: Sep. 13, 2005

(54) AUTOMATIC STONE-TRACKING SYSTEM

(76) Inventors: Shen-Min Liang, 7F-4, No. 88, Sec. 3, Chang Rong Road, Tainan (TW), 702; Ioannis Manousakas, No. 2, Lane 3, Alley 290, Shien-Chen Road, Ling-Ya District, Kaohsiung City (TW), 800; Yong-Ren Pu, No. 34, Da-Jen 2nd St., Kwei-Jen, Tainan County (TW), 711; Fan-Ming Yu, 5F-1, No. 88, Sec. 3, Chang Rong Road, Tainan (TW), 701; Chien-Chen Chang, No. 75, Feng-Chia Road, Pintung (TW), 701; Chin-Hsing Chen, Department of Electrical Engineering, National Cheng Kung University, No. 1, Ta-Hsueh Road, Tainan City (TW)

( * ) Notice: Subject to any disclaimer, the term of this patent is extended or adjusted under 35 U.S.C. 154(b) by 184 days.

(21) Appl. No.: 10/061,240

(22) Filed: Feb. 4, 2002

(65) Prior Publication Data
US 2003/0149352 A1 Aug. 7, 2003

(51) Int. Cl.[7] .................................. A61B 8/00
(52) U.S. Cl. .............. 600/437; 600/439; 600/445; 600/454; 600/465; 600/469; 600/1; 600/2; 600/3; 600/4
(58) Field of Search ................... 600/437, 439, 600/445, 454, 465, 469; 601/1–4

(56) References Cited

U.S. PATENT DOCUMENTS

| | | | | |
|---|---|---|---|---|
| 4,669,483 A | * | 6/1987 | Hepp et al. ............... | 600/439 |
| 4,805,622 A | * | 2/1989 | Riedlinger et al. ......... | 600/442 |
| 4,936,291 A | * | 6/1990 | Forssmann et al. ......... | 600/439 |
| 5,036,836 A | * | 8/1991 | Terai et al. .............. | 601/4 |
| 5,152,289 A | * | 10/1992 | Viebach et al. ............ | 600/439 |
| 5,301,659 A | * | 4/1994 | Brisson et al. ............ | 601/4 |
| 5,383,459 A | * | 1/1995 | Iwama et al. ............. | 600/439 |
| 6,036,661 A | * | 3/2000 | Schwarze et al. .......... | 601/4 |
| 6,093,148 A | * | 7/2000 | Fujimoto ................. | 600/439 |
| 6,394,955 B1 | * | 5/2002 | Perlitz .................. | 600/439 |

* cited by examiner

*Primary Examiner*—Brian L. Casler
*Assistant Examiner*—William C. Jung
(74) *Attorney, Agent, or Firm*—Rosenberg, Klein & Lee

(57) ABSTRACT

A tracking system for stone treatment by extracorporeal shock wave lithotripsy includes a data processing unit, a motion controller, a servo-moving platform, a stone image-processing module, a stone localization module, and a moving-mechanism control module. With the use of the stone-tracking system, the performance of an extracorporeal shock wave lithotriptor can be greatly improved, resulting in less side effect such as tissue damage.

5 Claims, 3 Drawing Sheets

AUTOMATIC STONE-TRACKING SYSTEM

BACKGROUND OF THE INVENTION

1. Field of the Invention

The present invention relates to an automatic stone-tracking system for stone treatment. In particular, the present invention relates to an automatic stone-tracking system that may locate the instant position of the stones, allowing subsequent accurate fragmentation of the stones without the risk of inadvertent injury to the tissues of the patient.

2. Description of the Related Art

In the recent twenty years, the extracorporeal shock wave lithotripsy (ESWL) has provided a new technique for the treatment of stones by a non-invasive fashion of surgery rather than a traditional invasive fashion. Although the ESWL has been widely used by urologists, the efficiency for stone fragmentation, estimated from the stone-free rate, is approximately 60–70% under urologist's monitoring during treatment. This is due to the calculus movement caused by patient's respiration during treatment, resulting in inaccurate targeting of shock waves. Up to date, there is no lithotriptor with highly accurate stone targeting in the international market of lithtriptors.

SUMMARY OF THE INVENTION

An objective of the present invention is to provide a real-time, automatic tracking system for stones so that the instant stone position of a patient can be localized and controlled by a lithotriptor.

A stone-tracking system in accordance with the present invention comprises a servo-motion unit, an ultrasound scanner, a motion controller, and a data processing unit. The servo-motion unit comprises a motion platform including an arc track, and a shock-wave reflector is mounted on the arc track. The ultrasound system comprises an ultrasound scanning probe mounted on the motion platform for localizing a position of a stone of a patient at any instant and sending information of the stone position. The motion controller is connected to the servo-motion unit for controlling the servo-motion unit. The data processing unit is connected to the ultrasound system and the motion controller. The data processing unit receives the information of the stone position from the ultrasound system and sends a signal to the motion controller in response to the information of the stone position to cause relative movement between the motion platform and a bed on which the patient lies until focus of the shock-wave reflector is coincident with the stone position.

The performance of the stone-tracking system was found to be very efficient on stone fragmentation.

Other objectives, advantages, and novel features of the invention will become more apparent from the following detailed description when taken in conjunction with the accompanying drawings.

DETAILED DESCRIPTION OF THE PREFERRED EMBODIMENT

Figure 1:
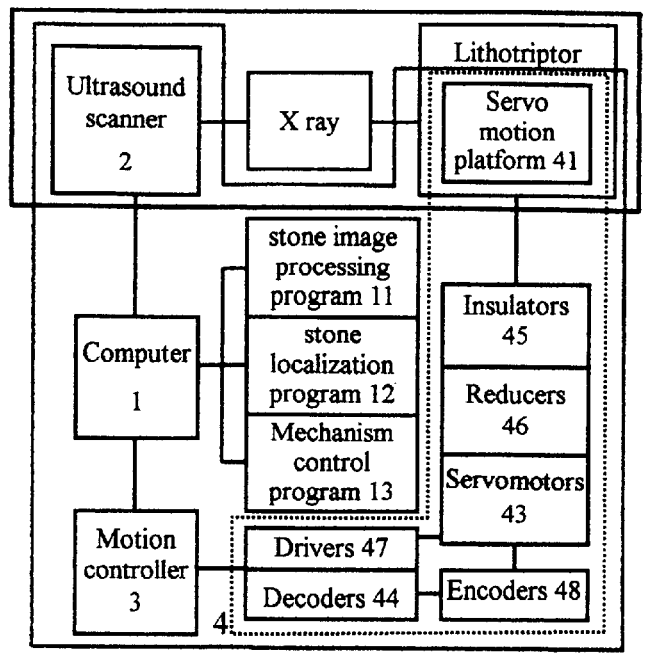
FIG. 1 is a block diagram of a stone-tracking system in accordance with the present invention.
Figure 2:
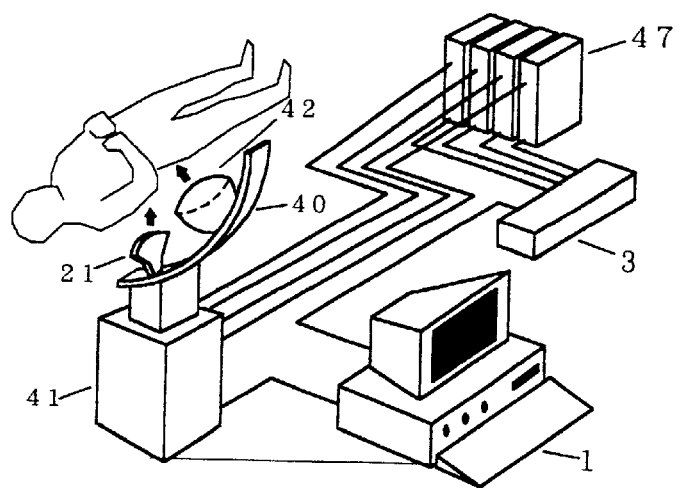
FIG. 2 is a schematic view of a servo-control system of the stone-tracking system used for stone treatment.

Referring to FIG. 1, an automatic stone-tracking system in accordance with the present invention comprises a data processing unit 1, an ultrasound system 2, a motion controller 3, and a servo motion unit 4. The term "stone" referred to herein means kidney calculi, ureteral calculi, bladder calculi, or any other calculi formed in a human body.

In this embodiment, the data processing unit 1 is a computer that is installed with a program 11 (module) of stone image processing, a program 12 (module) of stone localization, and a program 13 (module) for controlling a motion platform 41. The computer 1 is connected with the ultrasound scanner 2 and the motion platform 41.

Figure 3:
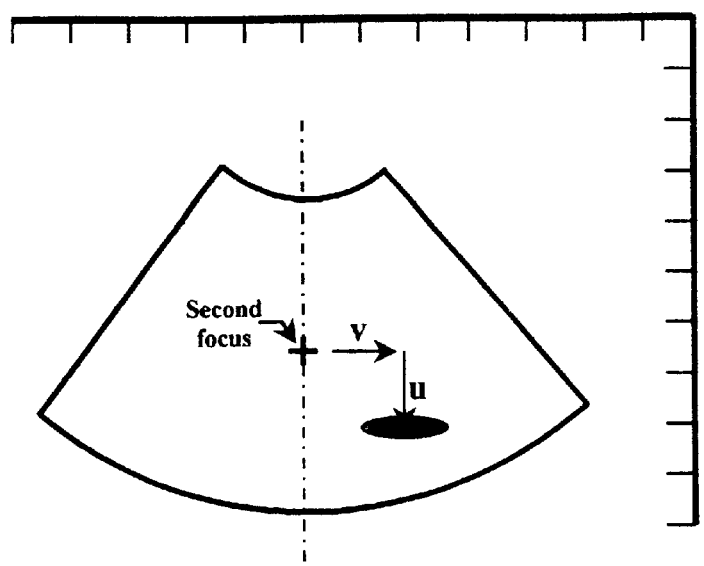
FIG. 3 is a schematic view illustrating stone displacement on the plane of an ultrasound stone image.
Figure 4:
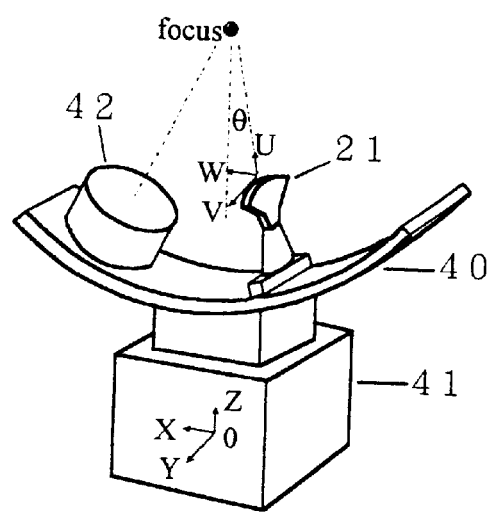
FIG. 4 is a schematic view illustrating the stone position, an ultrasound scanning probe, a shock-wave reflector, and a moving platform.
Figure 5:
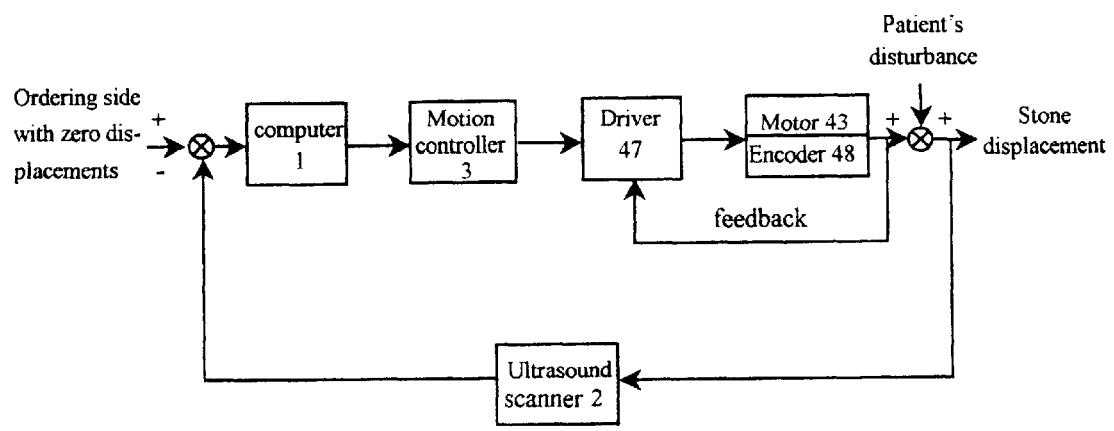
FIG. 5 is a schematic flow chart illustrating stone tracking for lithortripsy.

The ultrasound system 2 includes an ultrasound scanning probe 21 for localizing the stone position at any instant. The stone images are transmitted to the computer at a rate of about 10 images per second. Consequently, the stone displacements from the second focus of the shock-wave reflector 42, (U, V), due to patient's respiration are computed, as shown in FIG. 3. The first focus means the geometrical position of the shock wave reflector where the shock waves are produced. The second focus is the location where shock waves are focused to produce a high pressure enough for stone fragmentation. The term "focus" is referred herein as the geometrical position of the second focus of the ellipsoidal shock-wave reflector 42. The symbol θ denotes an inclination angle between the image plane and the YZ plane (X=0). The displacements of the motion platform 41 are related with the stone displacements by the following equation:

$$(\Delta X, \Delta Y, \Delta Z) = (U \sin \theta, V, U \cos \theta)$$

The displacements (ΔX,ΔY,ΔZ) will be transmitted to the motion controller 3. With the computed displacements (ΔX, ΔY,ΔZ) the motion controller 3 commands three drivers 47 to activate three servomotors 43 which subsequently move the motion platform 41. Thus a moving stone can be continuously localized to be within an effective pressure region for stone fragmentation.

In this embodiment, the motion controller 3 is an electronic board that is connected with three sets of motors 43 (preferably servomotors) and drivers 47 equipped with encoders 48 and three reducers 46. By using the control method of proportional integral and derivative, the motion controller 3 analyzes the motor locations and speeds from the encoders 48, and motivates the motors 43 and the reducers 46.

The servo motion unit 4 consists of a motion platform 41 with three-axis motion, three AC servomotors 43 with encoders 44, three reducers 46, and three insulators 45 (optionally). The servomotors 43, reducers 44, and insulators 46 are connected together. These three servomotors 43 are installed on the motion platform 41 and cause the motion platform 41 to do three-dimensional motion. The travel of each of the servomotors 43 is fed back to the motion controller 3. Each reducer 44 is provided to reduce the speed of the associated servomotors 43. Each insulator 45 is preferably Bakelite™ for isolating the associated servomotors 43 from the ground to thereby avoid interference and damage resulting from high voltage.

Lying on the motion platform 41 is the arc track 40 with a radius. The shock-wave reflector 42 and the ultrasound scanning probe 21 are mounted on the arc track 40. Since the arc center is the second focus of the shock-wave reflector 42, and always lies on the ultrasound image plane, a doctor (urologist) can judge whether the moving stone lies on the second focus by using the ultrasound images.

The stone localization module 12 is a computer program that computes the data of the instant stone location transmitted from the ultrasound system 2. The stone localization module 12 (program) provides the instant stone displacements from the second focus of the shock-wave reflector 42 for the motion controller 3. The stone localization module 12 consists of a transformation between the stone displacements on the image plane 41 and the displacements of the motion platform on a reference frame.

The stone image processing module 11 is a computer program that can determine the stone size and its center, and record the stone trajectory. The stone image processing module 11 (program) is developed by an automatic gray level threshold method that is based on the principle of gray level histogram entropy. The threshold is applied in a pre-selected region of interest that moves to follow the stone in real time.

The moving-mechanism control module 13 is a computer program that controls the motion of the motion platform 41 that moves in accordance to the stone displacements. The moving-mechanism control module 13 is used for the motion controller 3.

In an embodiment of the invention, the focus of the shock-wave reflector is moved to the stone position by means of moving the motion platform 41 when the stone is displaced as a result of respiration of the patient. In an alternative embodiment, the stone is moved to the focus of the shock-wave reflector 42 by means of moving the bed when the stone is displaced as a result of respiration of the patient on the bed.

It was verified that the performance of the improved lithotriptor with the stone-tracking system based on the efficiency of stone fragmentation. An in vitro study was made to verify the designed stone tracking system. The result of stone fragmentation with and without tracking conditions is shown in Table 1. It was found that the efficiency of lithotriptor with the stone-tracking system in accordance with the present invention is increased to 86% from 45% which was obtained at the conditions of no stone tracking and no doctor's monitoring.

Since the designed stone-tracking system is of real time, the second focus of the shock-wave reflector 42 can be instantly adjusted to the stone position during stone treatment. Consequently the patient's calculus can be accurately struck and fragmented by shock waves, resulting in less number of shock waves, less damage of the tissues in the vicinity of the stone, and less treatment time.

The following Table 1 shows comparison of efficiency of stone fragmentation with and without stone tracking.

| Sample | Without tracking (%) | With tracking (%) |
|---|---|---|
| 1 | 36.9 | 84.5 |
| 2 | 63.9 | 93.1 |
| 3 | 38.3 | 84.0 |
| 4 | 46.1 | 82.1 |
| 5 | 50.4 | 88.9 |
| 6 | 35.2 | 82.1 |
| 7 | 52.6 | 81.7 |
| 8 | 17.4 | 86.0 |
| 9 | 37.6 | 91.6 |
| 10 | 48.4 | 70.6 |
| 11 | 39.8 | 83.7 |
| 12 | 58.8 | 98.9 |
| 13 | 60.7 | 85.1 |
| Average ± SD | 45.1 ± 12.7 | 85.6 ± 6.8 |

The efficiency of stone fragmentation is defined as the ratio of the number of shock waves needed for fragmenting a fixed stone to the number of shock waves for a moving stone at the condition of requiring fragment sizes being less than 2 mm.

Although the invention has been explained in relation to its preferred embodiment, it is to be understood that many other possible modifications and variations can be made without departing from the scope of the invention as hereinafter claimed.

What is claimed is:

1. A stone-tracking system comprising:
   a servo-motion unit comprising a motion platform including an arc track, a shock-wave reflector being mounted on the arc track;
   an ultrasound scanner comprising an ultrasound scanning probe mounted on the motion platform for localizing a position of a patient's stone at any instant and generating information of stone position;
   a motion controller connected to the servo-motion unit for controlling the servo-motion unit; and
   a data processing unit connected to the ultrasound scanner and the motion controller, the data processing unit receiving the information indicative of stone position from the ultrasound scanner and automatically actuating the motion controller in adaptive manner responsive to the information indicative of stone position to cause relative movement between the motion platform and a bed on which the patient lies until a focus of the shock-wave reflector is coincident with the stone position, the data processing unit including a moving-mechanism control program that controls the motion of the motion platform to move in accordance with a displacement of a patient's stone.

2. The stone-tracking system as claimed in claim 1, wherein the servo-motion unit comprises (a) at least one servomotor mounted in the motion platform, a travel of the at least one servomotor being fed back to the motion controller, and (b) at least one reducer for reducing a speed of the at least one servomotor.

3. A stone-tracking system comprising:
   a servo-motion unit comprising a motion platform including an arc track, a shock-wave reflector being mounted on the arc track;
   an ultrasound scanner comprising an ultrasound scanning probe mounted on the motion platform for localizing a position of a patient's stone at any instant and generating information indicative of stone position;
   a motion controller connected to the servo-motion unit for controlling the servo-motion unit; and
   a data processing unit connected to the ultrasound scanner and the motion controller, the data processing unit receiving the information indicative of stone position from the ultrasound scanner and sending a signal to the motion controller in response to the information indicative of stone position to cause relative movement between the motion platform and a bed on which the patient lies until a focus of the shock-wave reflector is coincident with the stone position, the data processing unit including a stone image processing program that determines a size and a center of the stone and that records a trajectory of the stone, the program being developed by an automatic gray level threshold method that is based on the principle of gray level histogram entropy, the threshold being applied in a pre-selected region of interest that moves to follow the stone in real time.

4. A stone-tracking system comprising:

a servo-motion unit comprising a motion platform including an arc track, a shock-wave reflector being mounted on the arc track, and at least one motor mounted in the motion platform;

an ultrasound scanner comprising an ultrasound scanning probe mounted on the motion platform for localizing a position of a patient's stone at any instant and generating information indicative of stone position;

a motion controller connected to the servo-motion unit for controlling the servo-motion unit;

a data processing unit connected to the ultrasound scanner and the motion controller, the data processing unit receiving the information indicative of stone position from the ultrasound scanner and sending a signal to the motion controller in response to the information indicative of stone position to cause relative movement between the motion platform and a bed on which the patient lies until a focus of the shock-wave reflector is coincident with the stone position; and, at least one insulator to isolate said one motor from the shock-wave reflector, thereby avoiding interference and damage resulting from high voltage.

5. The stone-tracking system as claimed in claim 4, wherein said at least one insulator is phenol-formaldehyde composition.

* * * * *